US010083502B2

(12) United States Patent
Ryu et al.

(10) Patent No.: US 10,083,502 B2
(45) Date of Patent: Sep. 25, 2018

(54) COMPUTER AIDED DIAGNOSIS (CAD) APPARATUS AND METHOD

(71) Applicant: Samsung Electronics Co., Ltd., Suwon-si (KR)

(72) Inventors: Seung Woo Ryu, Seoul (KR); Seung Chul Chae, Seoul (KR); Jung Hoe Kim, Seongnam-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 194 days.

(21) Appl. No.: 14/950,543

(22) Filed: Nov. 24, 2015

(65) Prior Publication Data

US 2016/0148376 A1 May 26, 2016

(30) Foreign Application Priority Data

Nov. 26, 2014 (KR) .................. 10-2014-0166736

(51) Int. Cl.
*G06K 9/00* (2006.01)
*G06T 7/00* (2017.01)
(Continued)

(52) U.S. Cl.
CPC .............. *G06T 7/0012* (2013.01); *A61B 8/00* (2013.01); *A61B 8/085* (2013.01); *A61B 8/0825* (2013.01); *A61B 8/469* (2013.01); *A61B 8/5223* (2013.01); *G06K 9/6292* (2013.01); *A61B 5/055* (2013.01); *A61B 5/4312* (2013.01); *A61B 5/7264* (2013.01); *A61B 5/7485* (2013.01); *A61B 6/12* (2013.01); *A61B 6/467* (2013.01); *A61B 6/469* (2013.01); *A61B 6/502* (2013.01); *A61B 6/5217* (2013.01);
(Continued)

(58) Field of Classification Search
CPC ......... G06T 7/0012; G06T 2207/10081; G06T 2207/10088; G06K 9/6292; A61B 8/0825; A61B 8/469; A61B 8/5223; A61B 6/032; A61B 8/463
USPC ....................................... 382/131
See application file for complete search history.

(56) References Cited

U.S. PATENT DOCUMENTS 8,285,019 B2 * 10/2012 Raundahl ............... G06K 9/527
378/50
8,600,133 B2 * 12/2013 Buelow ................ G06T 7/0012
382/128

(Continued)

FOREIGN PATENT DOCUMENTS

JP 2008-541889 A 11/2008
KR 20070028878 A 3/2007
KR 20120072961 A 7/2012

*Primary Examiner* — Van D Huynh
(74) *Attorney, Agent, or Firm* — Jefferson IP Law, LLP

(57) ABSTRACT

Disclosed are Computer Aided Diagnosis (CAD) apparatus and method to combine information on sequential image frames and to provide a superior classification result for the ROI in the image frame. The CAD apparatus may include a Region of Interest (ROI) detector configured to detect an ROI from image frames, a categorizer configured to create groups of image frames having successive ROI sections from among the image frames based on a result of the detection, a classifier configured to classify an ROI detected from each of the image frames belonging to the groups, and a result combiner configured to combine classification results for the image frames belonging to each group from the groups and to calculate a group result for the each group.

20 Claims, 7 Drawing Sheets

(51) Int. Cl.
  *G06K 9/62* (2006.01)
  *A61B 8/00* (2006.01)
  *A61B 8/08* (2006.01)
  *A61B 5/00* (2006.01)
  *A61B 5/055* (2006.01)
  *A61B 6/12* (2006.01)
  *A61B 6/00* (2006.01)
  *A61B 8/14* (2006.01)

(52) U.S. Cl.
  CPC ....... *A61B 8/14* (2013.01); *G06T 2207/10016* (2013.01); *G06T 2207/10081* (2013.01); *G06T 2207/10088* (2013.01); *G06T 2207/10104* (2013.01); *G06T 2207/10132* (2013.01); *G06T 2207/20076* (2013.01); *G06T 2207/20081* (2013.01); *G06T 2207/20084* (2013.01); *G06T 2207/30096* (2013.01)

(56) References Cited

U.S. PATENT DOCUMENTS

| | | | |
|---|---|---|---|
| 2006/0274928 A1 | 12/2006 | Collins et al. | |
| 2010/0111392 A1* | 5/2010 | Valadez | G06K 9/3233 382/131 |
| 2011/0026798 A1* | 2/2011 | Madabhushi | G01R 33/56 382/131 |
| 2011/0164815 A1* | 7/2011 | Sharma | G06F 17/3025 382/165 |
| 2011/0268338 A1 | 11/2011 | Collins et al. | |
| 2012/0166211 A1 | 6/2012 | Park et al. | |

* cited by examiner

COMPUTER AIDED DIAGNOSIS (CAD) APPARATUS AND METHOD

CROSS-REFERENCE TO RELATED APPLICATION(S)

This application claims the benefit under 35 U.S.C. § 119(a) of Korean Patent Application No. 10-2014-0166736, filed on Nov. 26, 2014, in the Korean Intellectual Property Office, the entire disclosure of which is incorporated herein by reference for all purposes.

BACKGROUND

1. Field

The following description relates to a Computer Aided Diagnosis (CAD) technology.

2. Description of Related Art

A Computer Aided Diagnosis (CAD) assists medical professionals by analyzing medical images, i.e., ultrasonic images, and marking an abnormal area in each medical image based on the analysis. Because of their limited perception capabilities, it is difficult for humans to perform such diagnosis without errors. In addition, analyzing each medical image requires a large amount of time, great attention, and care. To address these drawbacks, the CAD system is designed to improve accuracy of diagnosis and alleviate the burden that medical professionals may feel during analysis.

Since the CAD system classifies each region of interest (ROI) detected from a different image frame, different classification results may be obtained regarding image frames of the same lesion. There is need for a technology that combines information on all image frames for each lesion and provides a single classification result for each lesion.

SUMMARY

In one general aspect, there is provided a Computer Aided Diagnosis (CAD) including a Region of Interest (ROI) detector configured to detect an ROI from image frames, a categorizer configured to create groups of image frames having successive ROI sections from among the image frames based on a result of the detection, a classifier configured to classify an ROI detected from each of the image frames belonging to the groups, and a result combiner configured to combine classification results for the image frames belonging to each group from the groups and to calculate a group resultfor the each group.

The categorizer may be further configured to group the plurality of image frames into a group based on an image frame where no ROI is detected.

A classification result obtained by the classifier may include at least one of BI-RADS Lexicon information or BI-RADS Category information on a corresponding ROI.

The result combiner may be further configured to calculate a score for each BI-RADS Lexicon item or each BI-RADS Category item in the each group based on the classification results obtained by the classifier, and to select a BI-RADS Lexicon item with the highest score or a BI-RADS Category item with the highest score as a group result.

The result combiner may be further configured to calculate the score for each BI-RADS Lexicon item or each BI-RADS Category item in the each group by adding up frame scores of image frames corresponding to each BI-RADS Lexicon item or each BI-RADS Category item in the group, and wherein the frame scores may represent weights assigned to each of the image frames.

The frame score may be calculated based on a size of an ROI detected from each of the image frames in the each group and a model fitness of the each of the image frames in the each group.

The result combiner may be further configured to generate a histogram of the group based on the calculated score for each BI-RADS Lexicon item or each BI-RADS Category item in the each group.

The result combiner may be further configured to determine whether an ROI of the each group is malignant or benign based on the BI-RADS Lexicon item with the highest score or the BI-RADS Category item with the highest score in the each group.

The CAD apparatus may include a similar image combiner configured to combine image frames satisfying a condition from among continuous image frames, and to select any one of the combined images as a representative image frame, wherein the result combiner may be further configured to use the representative image frame when combining the classification results.

The condition may include at least one of a condition where a change in size of an ROI is smaller than a threshold value and a condition where a maximum size of an ROI is smaller than a threshold size.

The CAD apparatus may include a similar group combiner configured to generate a histogram representing characteristics of an ROI of the each group, and to combine similar groups into one group using a histogram clustering algorithm.

The histogram clustering algorithm may include one of a Hierarchical Agglomerative Clustering algorithm and a Bhattacharyya Coefficient algorithm.

The CAD apparatus may include a display component configured to display the group classification result for the group on a screen.

The CAD apparatus may include a feature value extractor configured to extract a feature value from contour of the ROI detected from image frames, an area adjacent to the contour, or pixels inside the contour, and the classifier may be further configured to classify the ROI detected in each image frame based on comparing a feature value extracted from the ROI with a pre-stored diagnostic model.

In another general aspect, there is provided a Computer Aided Diagnosis (CAD) method including a processor performing operations of detecting a Region of Interest (ROI) from a plurality of image frames, grouping image frames having successive ROI sections from among the plurality of image frames based on a result of the detection, classifying an ROI detected from each of the image frames belonging to a group, and calculating a group result for the group by combining classification results for the image frames belonging to the group.

The grouping of image frames may include grouping the plurality of image frames with reference to an image frame where no ROI is detected.

The classifying of the ROI may include identifying at least one of BI-RADS Lexicon information or BI-RADS Category information on the ROI detected from each of the image frames.

The calculating of the group result may include calculating a score for each BI-RADS Lexicon item or each BI-RADS Category item in the image frames belonging to the group, and selecting a BI-RADS Lexicon item with the highest score or BI-RADS Category item with the highest score in the group as the result of classification for the group.

The calculating of the score for each BI-RADS Lexicon item or each BI-RADS Category item in the group may include calculating a frame score based on size of an ROI detected from each of the image frames and model fitness of each of the image frames, and calculating the score for each BI-RADS Lexicon item or each BI-RADS Category item in the group by adding up frame scores for image frames in the group.

The CAD method may include generating a histogram of the group based on the calculated score for each BI-RADS Lexicon item or each BI-RADS Category item in the group.

The CAD method may include combining image frames that satisfies a condition from among continuous image frames, and selecting any one of the combined image frames as a representative image frame, using the representative image frame in combining the classification results for the image frames belonging to the group, and wherein the condition may include at least one of a condition where a change in size of an ROI is less than a threshold value and a condition where a maximum size of an ROI is less than a threshold size.

The CAD method may include generating a histogram representing characteristics of an ROI of each group, and combining similar groups into one group using a histogram clustering algorithm.

The model fitness of the each of the image frames may correspond to a probability distribution of the each BI-RADS Lexicon item or each BI-RADS Category item.

In another general aspect, there is provided a Computer Aided Diagnosis (CAD) method including a processor performing operations of detecting a Region of Interest (ROI) from a plurality of image frames, grouping image frames having successive ROI sections from among the plurality of image frames based on an image frame where no ROI is detected, classifying an ROI detected from each of the image frames belonging to a group based on a feature of the ROI, and calculating a group result by combining classification results for the image frames belonging to the group.

The feature may be extracted from contour of the ROI detected from image frames, an area adjacent to the contour, or pixels inside the contour.

Other features and aspects may be apparent from the following detailed description, the drawings, and the claims.

Figure 1:
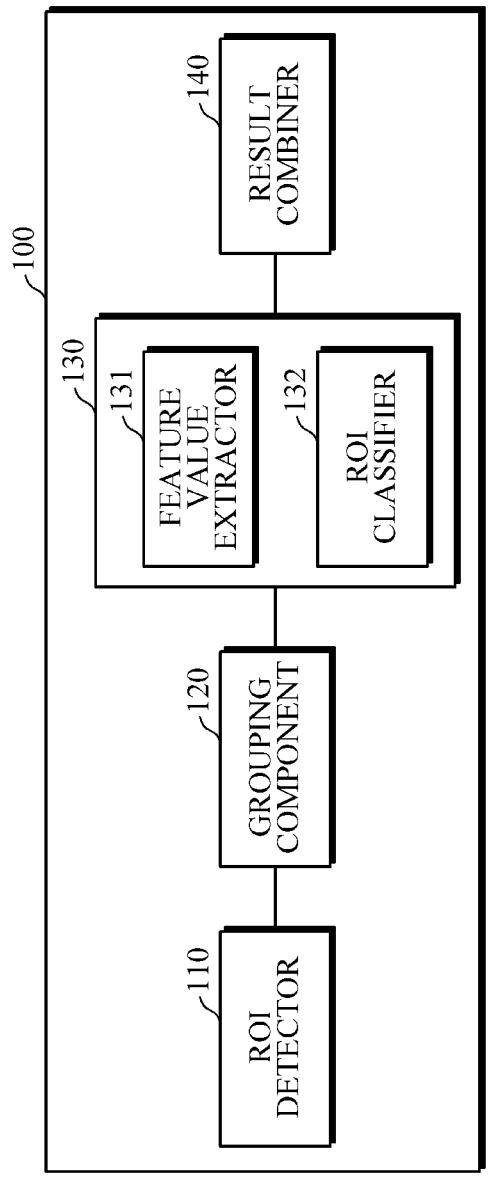
FIG. 1 is a diagram illustrating an example of a Computer Aided Diagnosis (CAD) apparatus.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses, and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

FIG. 1 is a diagram illustrating an example of a Computer Aided Diagnosis (CAD) apparatus. Referring to FIG. 1, a CAD apparatus 100 includes a region of interest (ROI) detector 110, a grouping component 120 (may also be referred to as a categorizer), a classifier 130, and a result combiner 140.

The ROI detector 110 may detect ROIs from a plurality of image frames using a lesion detection algorithm. An ROI may include not only a malignant lesion area, but also a lesion area that is not yet identified as either malignant or benign and a lesion area having unique features. The lesion detection algorithm may include algorithms such as, for example, AdaBoost, Deformable Part Models (DPM), Deep Neural Network (DNN), Convolutional Neural Network (CNN), and Sparse Coding. The plurality of image frames forms a sequence of continuously captured image frames, and may include images captured using equipment such as, for example, Computed Radiography (CR), Computed Tomography (CT), ultrasonic images, Magnetic Resonance Image (MRI), and Positron Emission Tomography (PET).

The grouping component 120 may group image frames having successive ROI sections from among a plurality of image frames into a group based on a result of ROI detection.

In an example, the grouping component 120 may group a plurality of image frames into different groups with reference to an image frame in which no ROI is detected. For example, among image frames 1 to 10, ROI A is detected from the image frames 1 to 4, ROI B is detected from the image frames 7 to 10, and no ROI is detected from the image frames 5 and 6. The grouping component 120 groups the image frames 1 to 4 with ROI A into group A, and the image frames 7 to 10 with ROI B into group B. ROI A and ROI B may be identical or different. The grouping component 120 may group image frames of the same ROI into different groups according to whether the ROI is continuously detected.

The classifier 130 may classify an ROI detected from an image frame of each group. According to an example, the classifier 130 may extract a feature value from an ROI detected from an image frame and classify the ROI based on the extracted feature value. The classifier 130 may include a feature value extractor 131 and an ROI classifier 132.

The feature value extractor 131 may extract a feature value from contour of an ROI detected from an image frame, an area adjacent to the contour, or information on pixels in the area inside the contour. A feature indicates a characteristic used to determine whether a corresponding area is a lesion area, and a feature value is a numeric value representing the feature. For example, in the case of breast imaging, according to Breast Imaging Reporting And Data System (BI-RADS) Lexicon classification a feature may be a lesion feature, such as, for example, shape, margin, echo pattern, orientation, boundary.

The feature value extractor 131 may be implemented using various image recognizing and machine learning algorithms, such as, for example, Deformable Part Model (DPM), Diabolo network, and Auto Encoder.

The ROI classifier 132 may classify an ROI in each image frame by comparing a feature value extracted from the ROI with a pre-stored diagnostic model. In a non-exhaustive example, a classification result for the ROI may include information such as, for example, BI-RADS Lexicon information, BI-RADS category information, and whether the ROI is malignant/benign.

The diagnostic model may be generated through machine learning using feature values extracted from a pre-collected diagnostic images. The generated diagnostic model may be stored in a database included in the determiner 130 or may be stored in an external database.

The machine learning algorithm may include algorithms such as, for example, artificial neural network, decision tree, Genetic Algorithm (GA), Genetic Programming (GP), Gauss Process Regression, Linear Discriminant Analysis, K-Nearest Neighbor(K-NN), perceptron, Radial Basis Function Network (RBFN), Support Vector Machine (SVM), and deep-learning.

The result combiner 140 may generate a group classification result for a group by combining classification results for image frames belonging to the group.

The result combiner 140 may calculate a score for each BI-RADS Lexicon item or each BI-RADS Category item in a group based on BI-RADS Lexicon information or BI-RADS Category information on an ROI detected from each image frame belonging to the group. The result combiner 140 may select a BI-RADS Lexicon item with the highest score or a BI-RADS Category item with the highest score as a group classification result for the group.

According to an example, a score for a BI-RADS Lexicon item or a BI-RADS Category item in a group may be the number of image frames corresponding to the BI-RADS Lexicon item or the BI-RADS Category item in the group. That is, the result combiner 140 may calculate a score for each BI-RADS Lexicon item or each BI-RADS Category item in the group by calculating the number of image frames corresponding to each BI-RADS Lexicon item or each BI-RADS Category item in the group.

For example, when group A consists of image frames 1 to 10, and image frames 1 and 10 are classified as BI-RADS Category 2, the image frames 2 and 9 are classified as BI-RADS Category 3, the image frames 3 to 6 are classified as BI-RADS Category 4A, and the image frames 7 and 8 are classified as BI-RADS Category 4B. The result combiner 140 may calculate the number of image frames corresponding to a BI-RADS Category item to be a score for the BI-RADS Category item. Thus, with respect to an ROI of the group A, the result combiner 140 may calculate a score of BI-RADS Category 2 to be 2, a score of BI-RADS Category 3 to be 2, a score for BI-RADS Category 4A to be 4, and a score for BI-RADS Category 4B to be 2.

According to another example, a score for an item may be defined as a sum of frame scores of image frames corresponding to the BI-RADS Lexicon item or the BI-RADS Category item, wherein the frame scores represent weights assigned to the image frames. The result combiner 140 may calculate a score for each BI-RADS Lexicon item or each BI-RADS Category item in a group by adding up weighted frame scores of image frames corresponding to each BI-RADS Lexicon item or each BI-RADS Category item in the group.

For example, when a frame score of each of the frames images 1, 2, 9, and 10 is 0.1, that a frame score of each of the image frames 3 and 8 is 0.3, and that a frame score of each of the image frames 4 to 7 is 0.5. In this case, the result combiner 140 calculate a score for each item by adding up frame scores of image frames corresponding to each BI-RADS Category item. With respect to the ROI of group A discussed above, the result combiner 140 may calculate a score for BI-RADS Category 2 to be 0.2, which is a sum of 0.1 (a frame score of the image frame 1) and 0.1 (a frame score of the image frame 10). The result combiner 140 may calculate a score for BI-RADS Category 3 to be 0.2, which is a sum of 0.1 (a frame score of the image frame 2) and 0.1 (a frame score of the frame image 9). The result combiner 140 may calculate a score for BI-RADS Category 4A to be 1.8 which is a sum of 0.3 (a frame score of the image frame 3), 0.5 (a frame score of the image frame 4), 0.5 (a frame score of the frame image 5), and 0.5 (a frame score of the image frame 6). The result combiner 140 may calculate a score for BI-RADS Category 4B to be 0.8, which is a sum of 0.5 (a frame score of the image frame 7) and 0.3 (a frame score of the image frame 8).

In an example, a frame score may be calculated by Equation 1 that is represented as below:

$$FS_n = \text{Fitness}_n \times NLS_n \qquad \text{[Equation 1]}$$

In Equation 1, n denotes a numeric value of an image frame, $NLS_n$ denotes a normalized size of an ROI detected from the $n^{th}$ image frame (e.g., a relative size of an ROI detected in the $n^{th}$ image frame with reference to the largest size of an ROI detected from an image frame group, or a normalized size of lesion), and $\text{Fitness}_n$ denotes model fitness of the $n^{th}$ image frame.

The model fitness may be a probability. For example, a lesion classification result regarding an image frame is given in a form of probability distribution. When the classification shows BI-RADS Category 1, 2, 3, 4A, 4B, and 5, only BI-RADS Category 1 may used as a final classification result if a probability of the image frame 1 to be BI-RADS Category 1 is 75%(0.75) and a probability to be BI-RADS Category 2 is 25%(0.25). To calculate a frame score (FS), probabilities regarding all the categories may be multiplexed.

Based on a score for each RADS Lexicon or BI-RADS Category item in a group, the result combiner 140 may generate a histogram of the image frame group, such as, for example, a Lexicon histogram or a Category histogram, as a group classification result for the image frame group.

The result combiner 140 may combine all classification results for image frames belonging to a group to determine whether an ROI of the group is malignant or benign in an attempt to calculate a group classification result for the group. For example, the result combiner 140 may determine whether an ROI of a group is malignant or benign based on a BI-RADS Lexicon item with the highest score or a BI-RADS Category item with the highest score in the group.

Figure 2:
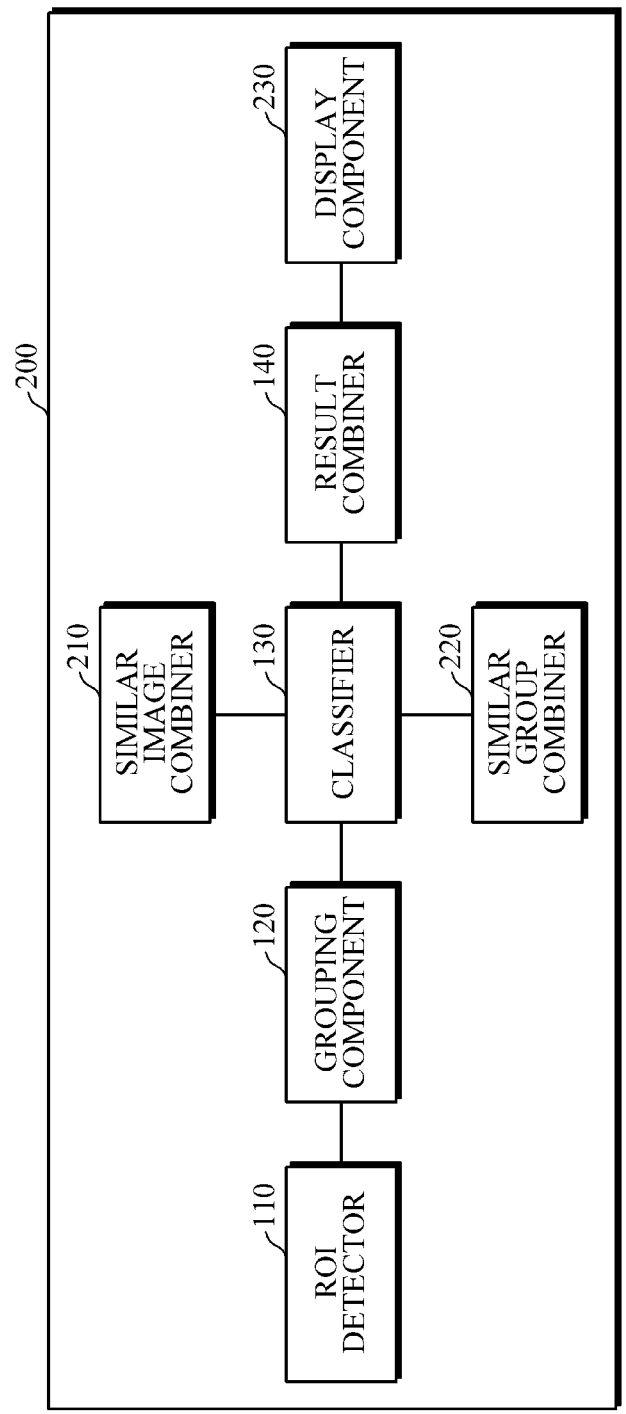
FIG. 2 is a diagram illustrating another example of a CAD apparatus.

FIG. 2 is a diagram illustrating another example of a CAD apparatus. Referring to FIG. 2, a CAD apparatus 200 may include a similar image combiner 210, a similar group combiner 220, and a display component 230, in addition to the configurations of the CAD apparatus 100 shown in FIG. 1. Many of the components shown in FIG. 2 have been described with reference to FIG. 1. The above description of FIG. 1, is also applicable to FIG. 2, and is incorporated herein by reference. Thus, the above description may not be repeated here.

The similar image combiner 210 may combine similar image frames that satisfy a predetermined condition among continuous image frames, and select any image frame of the combined similar image frames as a representative image frame. The predetermined condition may include a condition where a change in the size of an ROI needs to be smaller than a predetermined threshold and a condition where the maximum size of an ROI needs to be smaller than a predetermined threshold.

In this case, when combining all classification results, the result combiner 140 may use only the representative image frame among the combined similar image frames.

If a change in the size of an ROI or a maximum size of an ROI is too small, the ROI may be insignificant. Thus, by combining image frames with the insignificant ROI into a single image frame, it is possible to improve performance .

The similar group combiner 220 may combine similar groups into one group. Specifically, the similar group combiner 220 may generate a histogram representing characteristics of an ROI of each group, and combine similar groups into one group by using a histogram clustering algorithm. The characteristics of an ROI may be Lexicon information on the ROI, such as, for example, Round, Oval, Lobular, Microlobulated (irregular), Circumscribe, Indistinct, Spiculated, Fat containing, Density Low, Density Equal, and Density high.

For example, the similar group combiner 220 may combine similar groups into one group by using a Hierarchical Agglomerative Clustering algorithm, such as, for example, Hierarchical Agglomerative Clustering algorithm and a Bhattacharyya Coefficient algorithm.

As described above, the grouping component 120 may group image frames with the same ROI into groups based on whether the ROI is continuously detected. In this case, the same ROI may be classified redundantly and classification results thereof may be inconsistent. Thus, by combining similar groups into one group, it is possible to improve performance of the system.

The display component 230 may display a group classification result for each group on a screen. For example, the display component 230 may display information on a BI-RADS Lexicon item with the highest score or a BI-RADS Category item with the highest score in each group, a Lexicon or Category histogram of each group, and a determination as to whether an ROI of each group is malignant or benign.

Figure 3A:
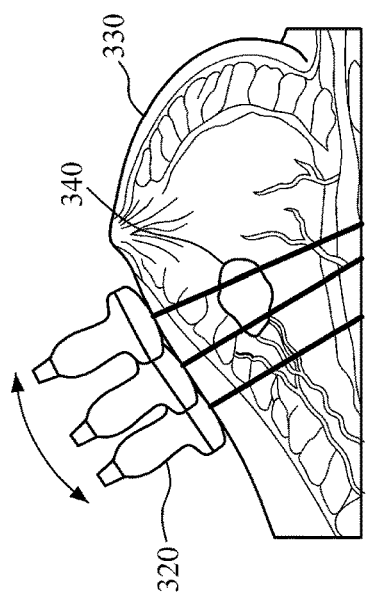
FIGS. 3A and 3B are diagrams illustrating examples for explaining detailed operations of a CAD apparatus.
Figure 3A:
Figure 3A:
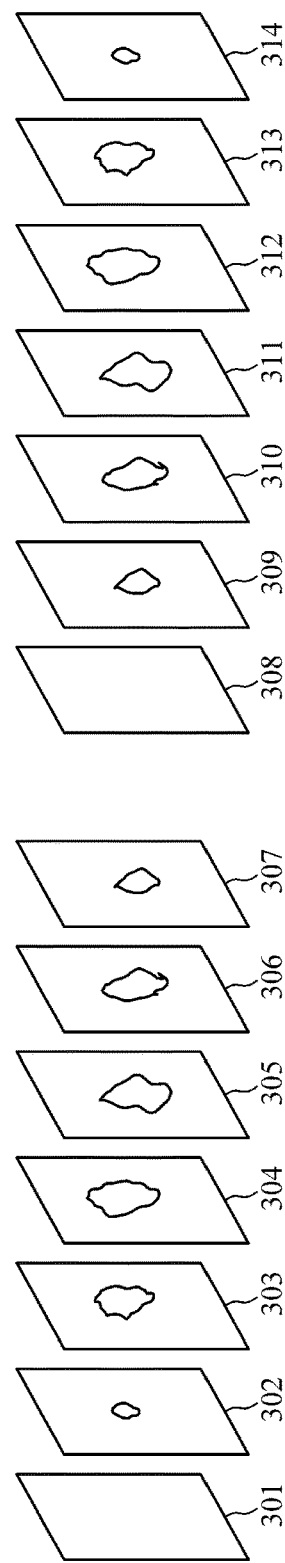
Figure 3B:
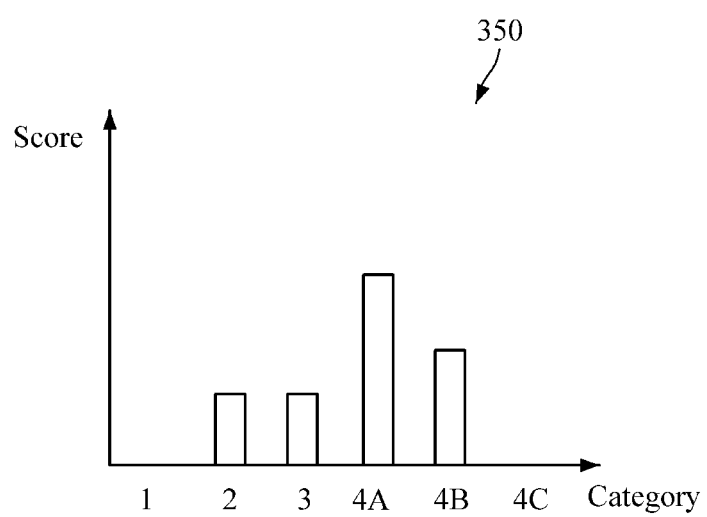

FIGS. 3A and 3B are diagrams illustrating examples of operations of a CAD apparatus.

Referring to FIGS. 3A and 3B, a user moves a probe 320 to the right and then to the left. In this case, with respect to a patient's specific body part 330, the CAD apparatus 200 acquires image frames 1 to 7 (301 to 307) sequentially when moving the probe 320 to the right, and image frames 8 to 14 (308 to 314) sequentially when moving the probe 320 to the left.

Once the image frames 1 to 14 (301 to 314) are acquired, the ROI detector 110 may detect an ROI 340 from each of the image frames 1 to 14 (301 to 314). An ROI is detected from the image 2 to 7 (302 to 307) and the image frames 9 to 14 (309 to 314), but no ROI is detected from the images 1 and 8.

With reference to the image frame 1 (301) and the image frame 8 (308), the grouping component 120 may group the image frames 2 to 7 (302 to 307) and the image frames 9 to 14 (309 to 314) into two different groups. The grouping component 120 may group the image frames 2 to 7 (302 to 307) into group A, and the image frames 9 to 14 (309 to 314) into group B.

With respect to image frames (302 to 307 and 309 to 314) of each group (group A and group B), the classifier 130 may classify an ROI detected from each image frame. In FIGS. 3A and 3B, image frame 2 (302) and 14 (314) are classified as BI-RADS Category 2; image frames 7 (307) 9 (309) are classified as BI-RADS Category 3; image frames 3 (303), 4 (304), 6 (306), 10 (310) and 13 (313) are classified as BI-RADS Category 4A; and image frames 5 (305), 11 (311) and 12 (312) are classified as BI-RADS Category 4B.

The similar group combiner 220 may combine similar groups, such as group A and group B, into one group. In FIGS. 3A and 3B, image frames (302 to 307) in group A and image frames (309 to 314) in group B are images capturing the same ROI. Characteristics of the ROI of group A and characteristics of the ROI of group B are similar, and thus, the similar group combiner 220 combines group A and group B into one group.

The result combiner 140 may calculate a score for each BI-RADS Category item in each group based on BI-RADS Category information of each image frame (302 to 307 and 309 to 314) in the combined group, and generate a histogram, as shown in FIG. 3B, based on the calculated scores. In FIGS. 3A and 3B, a score for BI-RADS Category 2 and BI-RADS Category 3 is calculated to be 2, a score for Category 4A is calculated to be 5, and a score for Category 4B is calculated to be 3. Based on the calculated scores, the result combiner 140 generates a Category histogram 350 of the combined group.

Figure 4:
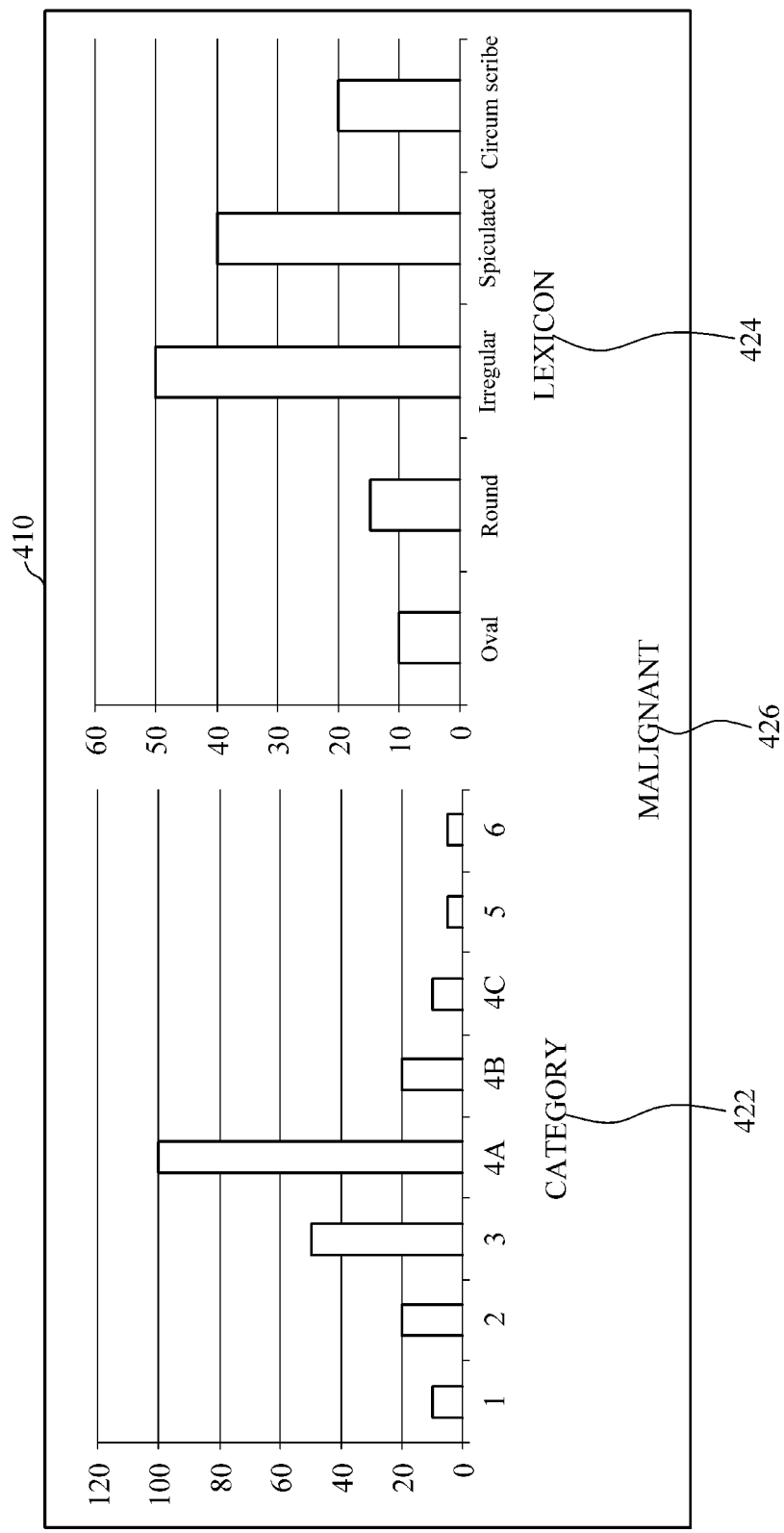
FIG. 4 is a diagram illustrating an example of a final classification result on a screen.

FIG. 4 is a diagram illustrating an example of a group classification result displayed on a screen. Referring to FIG. 4, as a group classification result for each group, the display component 230 may display, on the screen 410, a Lexicon histogram 424 of each group, a Category histogram 422 of each group, and a determination 426 as to whether an ROI of each group is malignant or benign.

The information displayed by the display component 230 on the screen 410 are non-exhaustive illustration, and other arrangements and types of information are considered to be well within the scope of the present disclosure. For example, the display component 230 may display, on the screen 410, information on a BI-RADS Lexicon item with the highest score or a BI-RADS Category item with the highest score in each group.

Figure 5:
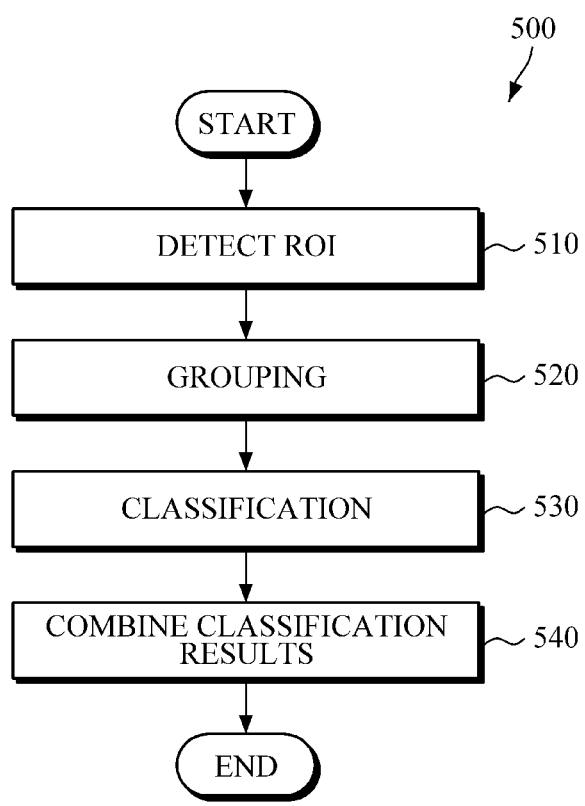
FIG. 5 is a diagram illustrating an example of a CAD method.

FIG. 5 is a diagram illustrating an example of a CAD method. The operations in FIG. 5 may be performed in the sequence and manner as shown, although the order of some operations may be changed or some of the operations omitted without departing from the spirit and scope of the illustrative examples described. Many of the operations shown in FIG. 5 may be performed in parallel or concurrently. The above description of FIGS. 1-4, is also applicable to FIG. 5, and is incorporated herein by reference. Thus, the above description may not be repeated here.

In 510, a CAD method 500 includes detecting ROIs from a plurality of image frames. For example, the CAD apparatus 100 may detect ROIs from a plurality of image frames using a lesion detection algorithm such as, for example, AdaBoost, DPM, DNN, CNN, and Sparse Coding.

In 520, a plurality of image frames having successive ROI sections are grouped into one group based on the result of the ROI detection. For example, the CAD apparatus 100 may group a plurality of image frames into groups with reference to an image frame in which no ROI is detected. In this case, even image frames from which the same ROI is detected may be grouped into different groups according to whether the ROI is continuously detected.

In 530, an ROI detected from each image frame of each group is classified. For example, the CAD apparatus 100 may extract a feature value from an ROI detected from each image frame, and classify the detected ROI based on the extracted feature value. The classification result regarding the ROI may include information such as, for example, BI-RADS Lexicon information on the ROI, BI-RADS Category information on the ROI, and whether the ROI is malignant/benign.

In 540, the CAD apparatus 100 calculates a group classification result for a group by combining all classification results for image frames belonging to the group.

For example, the CAD apparatus 100 may calculate a score for each BI-RADS Lexicon item or each BI-RADS Category item in a group based on BI-RADS Lexicon information or BI-RADS Category information on an ROI detected from each image frame in the group. The CAD apparatus 100 may select a BI-RADS Lexicon item with the highest score or a BI-RADS Category item with the highest score as a group classification result for the group. The score for each item may be obtained by calculating the number of image frames corresponding to each BI-RADS Lexicon item or each BI-RADS Category item or by adding up frame scores of image frames corresponding to each BI-RADS Lexicon item or each BI-RADS Category item. A frame score may be calculated by Equation 1 above.

In another example, the CAD apparatus 100 may generate a histogram (Lexicon histogram or Category histogram) of a group as a group classification result for the group based on a score for each BI-RADS Lexicon item or each BI-RADS Category item in the group.

In yet another example, the CAD apparatus 100 may combine all classification results for image frames belonging to the group to determine whether an ROI of a group is malignant or benign in an effort to calculate a group classification result for the group.

Figure 6:
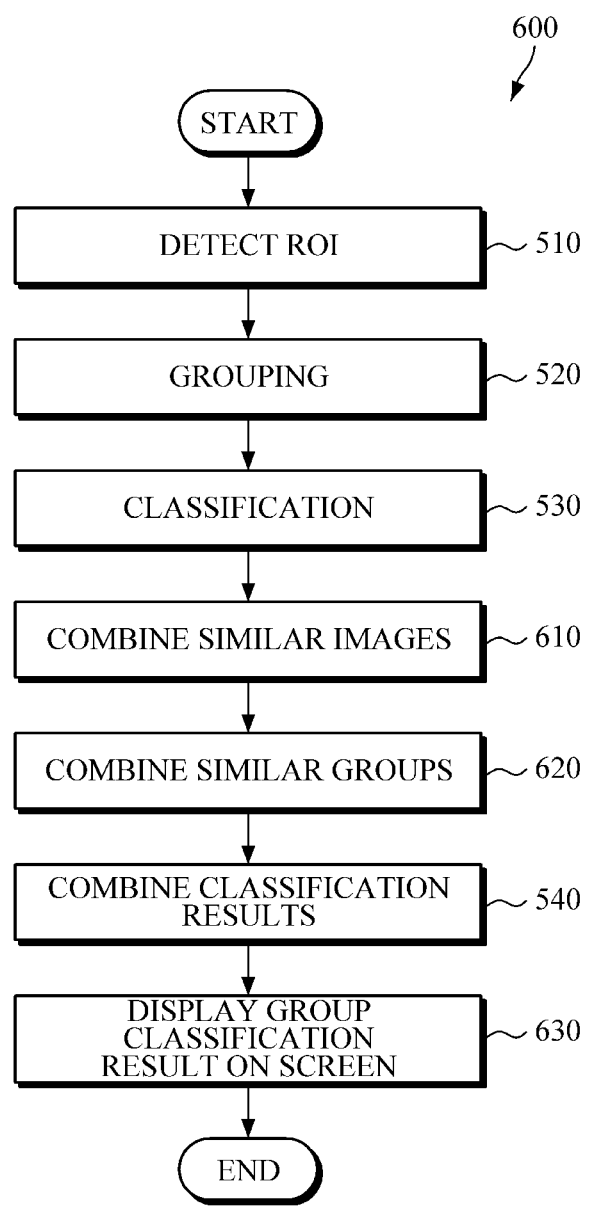
FIG. 6 is a diagram illustrating another example of a CAD method.

FIG. 6 is a diagram illustrating another example of a CAD method. The operations in FIG. 6 may be performed in the sequence and manner as shown, although the order of some operations may be changed or some of the operations omitted without departing from the spirit and scope of the illustrative examples described. Many of the operations shown in FIG. 6 may be performed in parallel or concurrently. The above description of FIGS. 1-5, is also applicable to FIG. 6, and is incorporated herein by reference. Thus, the above description may not be repeated here.

Referring to FIG. 6, a CAD method 600 may further include combining similar images in 610, combining similar groups in 620, and displaying a result on a screen in 630, in addition to operations shown in the CAD method 500.

In 610, similar image frames satisfying a predetermined condition from among continuous image frames are combined. For example, the CAD apparatus 200 combines similar image frames satisfying a predetermined condition from among continuous image frames, and selects any image frame from among the combined similar image frames as a representative image frame. The predetermined condition may include conditions such as, for example, a condition where a change in the size of an ROI needs to be smaller than a predetermined threshold and a condition where the maximum size of an ROI needs to be smaller than a predetermined threshold.

If a change in the size of an ROI or the maximum size of an ROI is too small, the ROI may be insignificant. Thus, by combining all the image frames including the insignificant ROI into one image frame, it is possible to improve performance of the system.

In 620, similar groups are combined into one group. For example, the CAD apparatus 200 may generate a histogram representing characteristics of an ROI of each group, and combine similar groups into one group using a histogram clustering algorithm, such as, for example, a Hierarchical Agglomerative Clustering algorithm, and a Bhattacharyya Coefficient algorithm. The characteristics of an ROI may be Lexicon information of the ROI, such as, for example, Round, Oval, Lobular, Microlobulated (irregular), Circumscribe, Indistinct, Spiculated, Fat containing, Density Low, Density Equal, and Density high.

As described above regarding operation 520, even image frames from which the same ROI is detected may be classified into different groups according to whether the ROI is continuously detected. In this case, the same ROI may be classified redundantly and classification results thereof may be inconsistent. Thus, by combining similar groups into one group, it is possible to improve performance of the system.

In 630, a group classification result for each group may be displayed on a screen. For example, the CAD apparatus 200 may display, on a screen, information such as, for example, a BI-RADS Lexicon item with the highest score or a BI-RADS Category item with the highest score in each group, Lexicon histogram or Category histogram for each group, and whether an ROI of each group is malignant/benign.

The apparatuses, units, modules, devices, and other components illustrated that perform the operations described herein are implemented by hardware components. Examples of hardware components include controllers, sensors, generators, drivers and any other electronic components known to one of ordinary skill in the art. In one example, the hardware components are implemented by one or more processors or computers. A processor or computer is implemented by one or more processing elements, such as an array of logic gates, a controller and an arithmetic logic unit, a digital signal processor, a microcomputer, a programmable logic controller, a field-programmable gate array (FPGA), a programmable logic array, a microprocessor, an application-specific integrated circuit (ASIC), or any other device or combination of devices known to one of ordinary skill in the art that is capable of responding to and executing instructions in a defined manner to achieve a desired result. In one example, a processor or computer includes, or is connected to, one or more memories storing instructions or software that are executed by the processor or computer. Hardware components implemented by a processor or computer execute instructions or software, such as an operating system (OS) and one or more software applications that run on the OS, to perform the operations described herein. The hardware components also access, manipulate, process, create, and store data in response to execution of the instructions or software. For simplicity, the singular term "processor" or "computer" may be used in the description of the examples described herein, but in other examples multiple processors or computers are used, or a processor or computer includes multiple processing elements, or multiple types of processing elements, or both. In one example, a hardware component includes multiple processors, and in another example, a hardware component includes a processor and a controller. A hardware component has any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 5-6 that perform the operations described herein are performed by a processor or a computer as described above executing instructions or software to perform the operations described herein.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In another example, the instructions or software include higher-level code that is executed by the processor or computer using an interpreter. Programmers of ordinary skill in the art can readily write the instructions or software based on the block diagrams and the flow charts illustrated in the drawings and the corresponding descriptions in the specification, which disclose algorithms for performing the operations performed by the hardware components and the methods as described above.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A Computer Aided Diagnosis (CAD) apparatus comprising:
    a memory configured to store instructions;
    at least one processor, upon executing the stored instructions, configured to:
        detect a Region of Interest (ROI) from a plurality of image frames,
        create at least one group of image frames based on a result of the detection, wherein the at least one group comprises successive image frames in which the ROI is detected, from among the plurality of image frames,
        extract a feature value from at least one of a contour of the ROI comprised in the successive image frames, an area adjacent to the contour, or pixels inside the contour,
        classify the ROI comprised in each of the successive image frames belonging to the at least one group by comparing the extracted feature value with a pre-stored diagnostic model,
        combine classification results for the successive image frames belonging to each group from the at least one group, and
        calculate a group result for the each group based on a result of the combination; and
    a display configured to display the group result on a screen.

2. The CAD apparatus of claim 1, wherein the at least one processor is further configured to group the plurality of successive image frames into a group based on an image frame where no ROI is detected.

3. The CAD apparatus of claim 1, wherein the classification result comprises at least one of BI-RADS Lexicon information or BI-RADS Category information on a corresponding ROI.

4. The CAD apparatus of claim 3, wherein the at least one processor is further configured to:
    calculate a score for each BI-RADS Lexicon item or each BI-RADS Category item in the each group based on the classification results, and
    select a BI-RADS Lexicon item with the highest score or a BI-RADS Category item with the highest score as the group result.

5. The CAD apparatus of claim 4,
    wherein the at least one processor is further configured to:
        calculate the score for each BI-RADS Lexicon item or each BI-RADS Category item in the each group by adding up frame scores of image frames corresponding to each BI-RADS Lexicon item or each BI-RADS Category item in the group, and
    wherein the frame scores represent weights assigned to each of the image frames.

6. The CAD apparatus of claim 5, wherein the frame score is calculated based on a size of an ROI detected from each of the successive image frames in the each group and a model fitness of the each of the successive image frames in the each group.

7. The CAD apparatus of claim 4, wherein the at least one processor is further configured to generate a histogram of the group based on the calculated score for each BI-RADS Lexicon item or each BI-RADS Category item in the each group.

8. The CAD apparatus of claim 4, wherein the at least one processor is further configured to determine whether an ROI of the each group is malignant or benign based on the BI-RADS Lexicon item with the highest score or the BI-RADS Category item with the highest score in the each group.

9. The CAD apparatus of claim 1, wherein the at least one processor is further configured to:
combine image frames satisfying a condition from among the successive image frames,
select any one of the combined images as a representative image frame, and
use the representative image frame when combining the classification results.

10. The CAD apparatus of claim 9, wherein the condition comprises at least one of a condition where a change in size of an ROI is smaller than a threshold value or a condition where a maximum size of an ROI is smaller than a threshold size.

11. The CAD apparatus of claim 1, wherein the at least one processor is further configured to:
generate a histogram representing characteristics of an ROI of the each group, and
combine similar groups into one group using a histogram clustering algorithm.

12. The CAD apparatus of claim 11, wherein the histogram clustering algorithm comprises one of a Hierarchical Agglomerative Clustering algorithm and a Bhattacharyya Coefficient algorithm.

13. A Computer Aided Diagnosis (CAD) method comprising:
detecting a Region of Interest (ROI) from a plurality of image frames;
grouping successive image frames in which the ROI is detected, from among the plurality of image frames based on a result of the detection;
extracting a feature value from at least one of a contour of the ROI comprised in the successive image frames, an area adjacent to the contour, or pixels inside the contour;
classifying the ROI comprised in each of the successive image frames belonging to a group by comparing the extracted feature value with a pre-stored diagnostic model;
calculating a group result for the group by combining classification results for the successive image frames belonging to the group; and
displaying the group result on a display.

14. The CAD method of claim 13, wherein the grouping of the plurality of image frames comprises grouping the plurality of successive image frames with reference to an image frame where no ROI is detected.

15. The CAD method of claim 13, wherein:
the classifying of the ROI comprises identifying at least one of BI-RADS Lexicon information or BI-RADS Category information on the ROI comprised in each of the successive image frames, and
the calculating of the group result comprises:
calculating a score for each BI-RADS Lexicon item or each BI-RADS Category item in the successive image frames belonging to the group; and
selecting a BI-RADS Lexicon item with the highest score or BI-RADS Category item with the highest score in the group as the group result.

16. The CAD method of claim 15, wherein the calculating of the score for each BI-RADS Lexicon item or each BI-RADS Category item comprises:
calculating a frame score based on size of an ROI comprised in each of the successive image frames and model fitness of each of the successive image frames; and
calculating the score for each BI-RADS Lexicon item or each BI-RADS Category item in the group by adding up frame scores for image frames corresponding to each BI-RADS Lexicon item or each BI-RADS Category item in the group.

17. The CAD method of claim 15, further comprising generating a histogram of the group based on the calculated score for each BI-RADS Lexicon item or each BI-RADS Category item in the group.

18. The CAD method of claim 13, further comprising:
combining image frames that satisfy a condition from among the successive image frames, and selecting any one of the combined image frames as a representative image frame, and
using the representative image frame in combining the classification results for the successive image frames belonging to the group,
wherein the condition comprises at least one of a condition where a change in size of an ROI is less than a threshold value or a condition where a maximum size of an ROI is less than a threshold size.

19. The CAD method of claim 13, further comprising:
generating a histogram representing characteristics of an ROI of each group; and
combining similar groups into one group using a histogram clustering algorithm.

20. The CAD method of claim 16, wherein the model fitness of the each of the successive image frames corresponds to a probability distribution of the each BI-RADS Lexicon item or each BI-RADS Category item.

* * * * *